United States Patent
Liu et al.

(10) Patent No.: US 8,809,366 B2
(45) Date of Patent: Aug. 19, 2014

(54) THIENOPYRIDINE ESTER DERIVATIVE CONTAINING CYANO GROUP, PREPARATION METHOD, USE AND COMPOSITION THEREOF

(71) Applicant: Tianjin Institute of Pharmaceutical Research, Tianjin (CN)

(72) Inventors: Dengke Liu, Tianjin (CN); Ying Liu, Tianjin (CN); Nan Yue, Tianjin (CN); Furong Chen, Tianjin (CN); Chubing Tan, Tianjin (CN); Yunsong Zhou, Tianjin (CN); Peng Liu, Tianjin (CN); Yigui Zhao, Tianjin (CN); Deguang Zhi, Tianjin (CN); Mo Liu, Tianjin (CN); Bingni Liu, Tianjin (CN); Changjiang Huang, Tianjin (CN); Lida Tang, Tianjin (CN)

(73) Assignee: Tianjin Institute of Pharmaceutical Research, Tianjin (TW)

( * ) Notice: Subject to any disclaimer, the term of this patent is extended or adjusted under 35 U.S.C. 154(b) by 0 days.

(21) Appl. No.: 13/674,850

(22) Filed: Nov. 12, 2012

(65) Prior Publication Data
US 2013/0072521 A1  Mar. 21, 2013

Related U.S. Application Data

(63) Continuation of application No. PCT/CN2011/000492, filed on Mar. 23, 2011.

(51) Int. Cl.
*A01N 43/00* (2006.01)
*A61K 31/33* (2006.01)
*A01N 43/42* (2006.01)
*A61K 31/44* (2006.01)

(52) U.S. Cl.
USPC .......................................... 514/301; 514/183

(58) Field of Classification Search
None
See application file for complete search history.

(56) References Cited

U.S. PATENT DOCUMENTS 4,051,141 A   9/1977   Castaigne
4,400,384 A * 8/1983   Amselem et al. ............. 514/301

FOREIGN PATENT DOCUMENTS

| CN | 101402641 A | 4/2009 |
|---|---|---|
| CN | 101693718 A | 4/2010 |
| EP | 0 542 411 A2 | 5/1993 |
| GB | 1 561 504 | 2/1980 |
| WO | WO2011029456 A1 | 3/2011 |
| WO | WO2011140816 A1 | 11/2011 |

OTHER PUBLICATIONS

Kumashiro et al., "Antiplatelet Aggregators Inhibit Development of Stress Ulcers in Sprague-Dawley Rats," Eur Surg Res., 1985; 17(1):44-52 (Abstract).*
Communication from European Patent Office regarding European Application 11780039.1, which is national phase application of PCT/CN2011000492, which is the parent application of current U.S. Continuation Application, Communication dated Jan. 31, 2013.
Extended Search Report from European Patent Office regarding European Application 11780039.1, which is national phase application of PCT/CN2011000492, which is the parent application of current U.S. Continuation Application, Extended Search Report dated Aug. 5, 2013.
Zhou Yun-song, et al. Synthesis of thienopyridine derivatives and its anti-platelet activity in vivo. Acta Pharmaceutica Sinica, 2011, 46 (1): 70-74. (with English Abstract only).
International Search Report on International Application PCT/CN2011/000492 (Publication WO2011140816A1), mailed Jun. 30, 2011.

* cited by examiner

*Primary Examiner* — Craig Ricci
*Assistant Examiner* — Jared D Barsky
(74) *Attorney, Agent, or Firm* — Harvest IP Law LLP

(57) ABSTRACT

A compound with the structure of the formula (I) or a pharmaceutically acceptable salt, a preparation method and use thereof are disclosed in the present invention, wherein R is cyano group. The compound provided by the present invention has an antiplatelet aggregation activity and can be used in preparing a medicament for preventing or treating cardiac and cerebral vascular diseases such as coronary artery syndromes, myocardial infarction and myocardial ischemia which are caused by platelet aggregation.

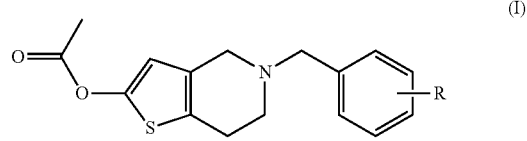

(I)

5 Claims, No Drawings

THIENOPYRIDINE ESTER DERIVATIVE CONTAINING CYANO GROUP, PREPARATION METHOD, USE AND COMPOSITION THEREOF

CROSS REFERENCE TO RELATED APPLICATION

This application is a continuation application filed under 35 U.S.C. §111(a), claiming the benefit under 35 U.S.C. §120 and §365(c) of the International Application PCT/CN2011/000492, filed Mar. 23, 2011, it being further noted that foreign priory benefit is based on Chinese Patent Application 201010171152.X, filed May 13, 2010 in the State Intellectual Property Office of Peoples Republic of China, the disclosures of which are thereby incorporated by reference.

TECHNICAL FIELD

The present invention belongs to the field of medical technology, and relates to a kind of compound having the effect of antiplatelet aggregation, and preparation method and use thereof. More specifically, the present invention relates to a thienopyridine ester derivative containing cyano group, preparation method, and use thereof.

BACKGROUND ART

Thrombosis may lead to cardiac, cerebral and pulmonary circulation disorders such as acute myocardial infarction, apoplexy and pulmonary embolism etc., which threatens people's health and lives, and is also a common complication of surgical operations and a factor of reocclusion after interventional angioplasty. Although thrombolytic therapy, interventional therapy and even surgical treatment that were developed in recent years have made a remarkable progress in treating acute myocardial infarction and cerebral infarction, greatly improved the success rate of rescuing patients and significantly improved the quality of life, the disability rate of cardiac and cerebral vascular diseases is still up to 30%. Therefore, developing a new medicament for preventing and treating cardiac and cerebral vascular diseases becomes a focus of attention and study in recent years.

There are many factors resulting in thrombosis, for example, adhesion and aggregation of platelet on the surface of injured vascular wall, blood stasis, formation of thrombin caused by activation of clotting factor, low activity of plasmin etc. In these factors, platelet is the essential material for thrombosis; therefore, the inhibition of platelet aggregation plays an important role in the prevention and treatment of thrombosis. Adenosine diphosphate (ADP) is an important agonist for amplification of platelet activation and aggregation effect, and it has become an important approach to prevent pathological thrombosis (coronary heart disease, cerebrovascular disease, pulmonary embolism, thrombophlebitis etc.) and myocardial infarction, unstable angina pectoris, peripheral vascular disease, congestive heart failure and the like by blocking ADP receptor so as to inhibit the function of platelet.

Clopidogrel is a first-line clinical antiplatelet agent of ADP receptor inhibitor at present, which is developed based on structural modification of a conventional antiplatelet agent Ticlopidine. As soon as the product of Clopidogrel came into the market, it quickly occupied the market by virtue of its stronger antithrombotic effect and smaller ADR. However, during more than ten years of clinical practices, its side effects of TTP and hemolytic uremic syndrome (HUS) etc. have been discovered. It is noteworthy that Clopidogrel, while producing an antiplatelet pharmacological action, also exhibits side effect of bleeding tendency. Clopidogrel has a longer $T_{max}$ in therapeutic dose and slow onset, therefore, its administration dosage is hard to control, which would probably further increase the bleeding tendency. Meanwhile, as Clopidogrel is an oily substance with extremely weak alkalinity, it can be salified by reacting with a strong acid, and it is hard to purify. The salts of Clopidogrel are unstable under humid conditions, and its free base would be precipitated again, and due to its strong acidity, it is also limited to some extent in terms of formulation.

Then based on Clopidogrel, Daiichi Sankyo Company Limited of Japan and Eli Lilly and Company of USA co-developed a new antiplatelet agent Prasugrel, another ADP receptor inhibitor. Many researches have proved that Prasugrel is more active and have a faster onset of action than Clopidogrel, and the difference between patients' reactions to Prasugrel is smaller than to Clopidogrel. The results of clinical controlled experiment of Prasugrel with Clopidogrel indicated that Prasugrel is more effective in reducing mortality caused by non-fatal heart attacks and apoplexy, but leads to more bleeding in patients. Therefore, it is necessary to research and develop a new medicament with good safety and antiplatelet aggregation activity.

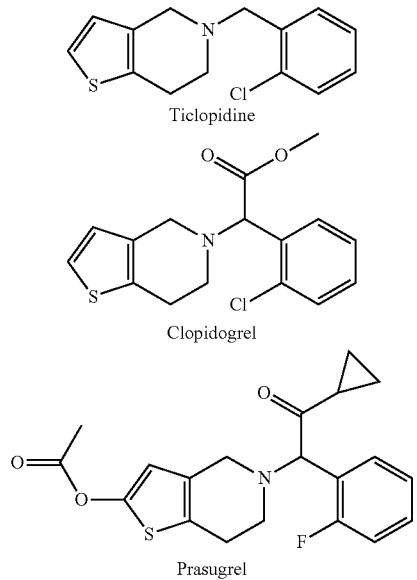

Synthetic methods and reviews concerning the thienopyridines compounds can be found in the following literatures: CN1683373, U.S. Pat. No. 4,681,888, U.S. Pat. No. 4,529,596, GB1501797, WO02059128, U.S. Pat. No. 4,174,448, GB1561504, WO2004094374, JP6135970 and JP63264588.

DESCRIPTION OF THE INVENTION

One object of the present invention is to provide a thienopyridine ester derivative containing cyano group.

Another object of the present invention is to provide a pharmaceutical composition comprising the above-mentioned thienopyridine ester derivative containing cyano group or a pharmaceutically acceptable salt thereof as a main active ingredient.

Yet another object of the present invention is to provide a method for preparing the above mentioned thienopyridine ester derivative containing cyano group and a pharmaceutically acceptable salt thereof.

Further object of the present invention is to provide a use of the above mentioned thienopyridine ester derivative containing cyano group and a pharmaceutically acceptable salt thereof in antiplatelet aggregation, especially a use in preparing a medicament for the prevention or treatment of cardiac and cerebral vascular diseases such as coronary artery syndromes, myocardial infarction, myocardial ischemia and the like which are caused by platelet aggregation.

The present invention provides a compound with the structure of general formula I and pharmaceutically acceptable salts thereof:

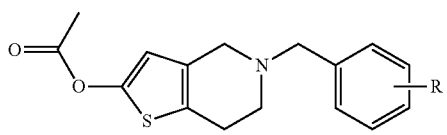

wherein, R is cyano group.

The compounds with the structure of formula I provided in the present invention are preferably the following compounds I-1, I-2 and I-3:

I-1: 5-(2-cyanobenzyl)-4,5,6,7-tetrahydrothieno[3,2-c]pyridin-2-yl acetate;
I-2: 5-(3-cyanobenzyl)-4,5,6,7-tetrahydrothieno[3,2-c]pyridin-2-yl acetate;
I-3: 5-(4-cyanobenzyl)-4,5,6,7-tetrahydrothieno[3,2-c]pyridin-2-yl acetate.

According to the present invention, there is provided a compound with the structure of formula I, wherein the pharmaceutically acceptable salt comprises the salts formed by the compound of formula I with an inorganic acid or an organic acid, wherein particularly preferred salts are: pharmaceutically acceptable salts such as hydrochlorides, hydrobromides, hydriodates, sulfates, hydrosulfates, phosphates, hydrophosphates, acetates, propionates, butyrates, lactates, mesylates, tosilates, maleates, benzoates, succinates, tartrates, citrates, fumarates, taurates, gluconates, and amino acid salts etc.

The present invention further provides a method for preparing the compound of formula I, and the specific preparation route is as follows:

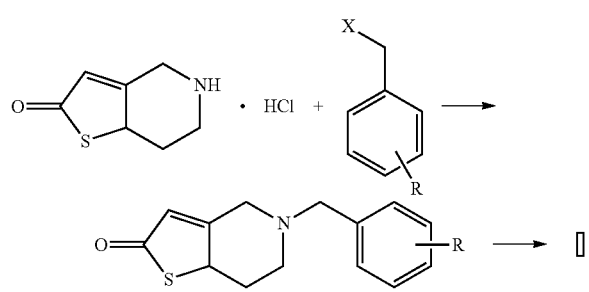

wherein, R is cyano group; X is bromine or chlorine.

Hydrochloride of thienopyridone is reacted with benzyl bromide or benzyl chloride substituted by cyano group at −10° C.-105° C. in the presence of an acid-binding agent, such as triethylamine, pyridine, potassium carbonate, sodium carbonate, sodium bicarbonate, potassium bicarbonate, sodium hydroxide or potassium hydroxide etc., in a solvent of dichloromethane, trichloromethane, acetonitrile or toluene etc. to prepare a key intermediate. The intermediate is further reacted with acetic anhydride, acetic acid, acetyl chloride or acetyl bromide etc., at −30° C.-65° C., in the presence of an acid-binding agent, such as triethylamine, pyridine, potassium carbonate, sodium carbonate, sodium bicarbonate, potassium bicarbonate, sodium hydroxide or potassium hydroxide etc., in a solvent of dichloromethane, trichloromethane or toluene, to prepare a target product I.

Various intermediates prepared in the reaction or the resulting product compound I can be dissolved into diethyl ether, DMF, acetone, methanol, ethanol, ethyl acetate or DMSO, and a solution of an inorganic acid or organic acid is added dropwise to prepare a pharmaceutically acceptable salt.

Specific operations can include: dissolving the intermediate or the resulting product compound I into diethyl ether, DMF, acetone, methanol, ethanol, ethyl acetate or DMSO, and adding a solution of hydrogen chloride in diethyl ether dropwise to the mixture in an ice-water bath until pH=2 to prepare a hydrochloride; or dissolving the compound into diethyl ether, DMF, acetone, methanol, ethanol, ethyl acetate or DMSO, adding equimolar taurine to the mixture, and heating and stirring the mixture to obtain a taurate; or dissolving the compound into diethyl ether, DMF, acetone, methanol, ethanol, ethyl acetate or DMSO, and adding concentrated sulfuric acid dropwise to the mixture in an ice-water bath until pH=3 to prepare a sulfate; etc.

The compound provided by the present invention is effective in treating human diseases which are caused by platelet aggregation. Although the compound of the present invention can be administrated directly without any preparation, the compound is preferred to be used in the form of pharmaceutical preparations. The administration route could be parenteral (such as intravenous or intramuscular) or oral administration.

The present invention further provide a use of the above mentioned compound having the structure of formula I or pharmaceutically acceptable salt thereof in antiplatelet aggregation, and a use of the above mentioned compound having the structure of formula I or pharmaceutically acceptable salt thereof in preparing a medicament for antiplatelet aggregation. Wherein, the medicament for antiplatelet aggregation is a medicament for treating or preventing cardiac and cerebral vascular diseases which are caused by platelet aggregation, wherein, the cardiac and cerebral vascular diseases can be coronary artery syndromes, myocardial infarction or myocardial ischemia.

The present invention further provide a pharmaceutical composition for antiplatelet aggregation, the pharmaceutical composition comprises therapeutically effective amount of the compound with the structure of formula I or pharmaceutically acceptable salt thereof according to the present invention, and a pharmaceutically acceptable carrier and/or excipient. According to the pharmaceutical composition of the present invention, wherein the pharmaceutical composition can be solid oral preparation, liquid oral preparation or injection.

The present invention still provide a method for treating cardiac and cerebral vascular diseases, the method comprises administrating a patient in need of the treatment therapeutically effective amount of the compound with the structure of formula I according to the present invention or administrating a patient in need of the treatment therapeutically effective amount of the pharmaceutical composition provided by the present invention.

The preparation method of the pharmaceutical composition of the compound of the present invention is as follows: combining the compound of the present invention with a pharmaceutical acceptable solid or liquid carrier using standard and conventional techniques, and optionally combining it with a pharmaceutical acceptable adjuvant and excipient to prepare microparticles or microspheres. The solid preparations comprise tablets, dispersed granules, capsules, sustained release tablets, sustained release pellets and the like. The solid carrier can be at least one material, which could serve as diluent, flavouring agent, solubilizer, lubricant, suspending agent, adhesive, disintegrating agent, or coating agent. Inert solid carriers include magnesium phosphate, magnesium stearate, talcum powder, lactose, pectin, propylene glycol, polysorbate 80, dextrin, starch, gelatin, cellulose materials such as methylcellulose and microcrystalline cellulose, low melting point paraffin, polyethylene glycol, mannitol, and cocoa butter etc. The liquid preparations include solutions, suspensions such as injections and powder etc.

The amount of the active ingredient (the compound of the present invention) contained in the pharmaceutical composition and unit dosage form could be specifically determined according to the patient's condition and the doctor's diagnosis, and the amount or concentration of the compound used could be adjusted in a wide range. Generally, the amount of the active compound is 0.5-90% by weight of the composition, preferably 0.5-70% by weight of the composition.

BEST MODE FOR CARRYING OUT THE INVENTION

The present invention will be further illustrated in detail with reference to the following examples, and the following examples only illustrate and explain the present invention and do not limit the scope of the present invention in any way. The compounds are tested by high performance liquid chromatography (HPLC) and thin-layer chromatography (TLC). The structures of the compounds could then be further confirmed by a test such as infrared spectroscopy (IR), nuclear magnetic resonance spectroscopy (1H NMR, 13C NMR), mass spectrometry (MS) and the like.

EXAMPLE 1

Preparation of Intermediate 1

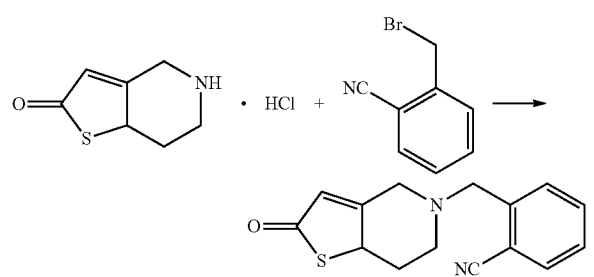

To a reaction flask equipped with a stirrer, a condenser and a thermometer was added 19.2 g of 5,6,7,7a-tetrahydrothieno[3,2-c]pyridin-2(4H)-one, which was then dissolved in 70 mL acetonitrile and cooled to −10° C. under stirring. 41.5 g of anhydrous potassium carbonate were added to the mixture. After addition of 19.6 g of 2-cyanobenzyl bromide to the reaction system in batches, the reaction mixture was heated to 45° C. and continued to react for 4 h (completion of the reaction was monitored by TLC). Then the reaction mixture was filtered and the solvent acetonitrile in the filtrate was evaporated to dryness. 50 mL of dichloromethane was added to the residue, and the mixture was washed with water (3×50 mL). The dichloromethane layer was separated, fully dried over anhydrous sodium sulfate, and filtered. The dichloromethane was evaporated off under reduced pressure to obtain 22.6 g yellow oil product (HPLC: 97.2%). Rf=0.47 [single point, developing solvent: v (petroleum ether): v (ethyl acetate)=1:2]. MS, m/Z: 270.0 (M).

EXAMPLE 2

Preparation of Intermediate 2

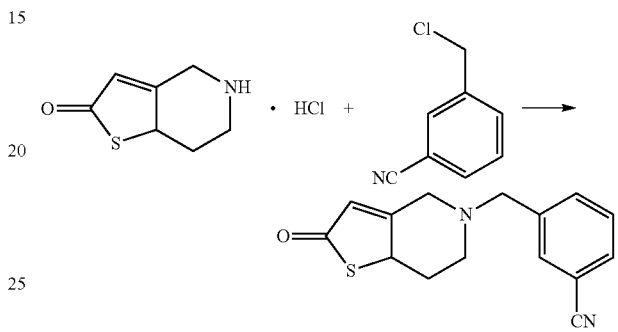

To a reaction flask equipped with a stirrer, a condenser and a thermometer was added 19.2 g of 5,6,7,7a-tetrahydrothieno[3,2-c]pyridin-2(4H)-one, which was then dispersed in 80 mL dichloromethane and cooled to 0° C. under stirring. 30.4 g of triethylamine were added to the mixture. After addition of 15.2 g of 3-cyanobenzyl bromide to the reaction system in batches, the reaction mixture was heated to reflux and continued to react for 5 h (completion of the reaction was monitored by TLC). The reaction liquid was washed with water (3×80 mL). Then the dichloromethane layer was separated, fully dried over anhydrous sodium sulfate, and filtered. The dichloromethane was evaporated off under reduced pressure to obtain 20.8 g light yellow solid product (HPLC: 96.4%). Rf=0.45 [single point, developing solvent: v (petroleum ether): v (ethyl acetate)=1:2]. MS, m/Z: 270.0 (M).

EXAMPLE 3

Preparation of Intermediate 3

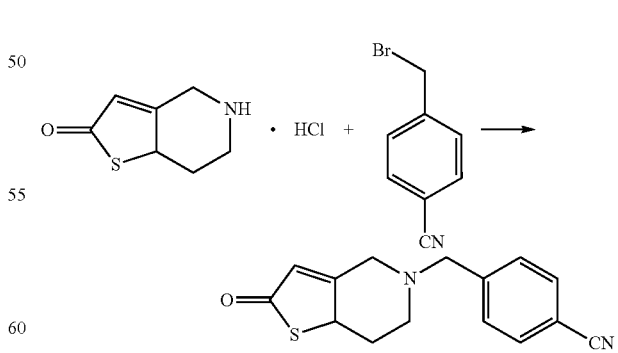

To a reaction flask equipped with a stirrer, a condenser and a thermometer was added 19.2 g of 5,6,7,7a-tetrahydrothieno[3,2-c]pyridin-2(4H)-one, which was then dispersed in 65 mL toluene and cooled to 10° C. under stirring. 23.7 g of pyridine were added to the mixture. After addition of 19.6 g of 4-cyanobenzyl bromide to the reaction system in batches, the reaction mixture was heated to 95° C. and continued to react for 2.5 h (completion of the reaction was monitored by TLC). The reaction mixture was washed with water (3×50 mL). Then the toluene layer was separated, fully dried over anhydrous sodium sulfate, and filtered. The toluene was evaporated off under reduced pressure to obtain 21.4 g yellow oil product (HPLC: 94.2%). Rf=0.41 [single point, developing solvent: v (petroleum ether): v (ethyl acetate)=1:2]. MS, m/Z: 270.0 (M).

EXAMPLE 4

(5-(2-cyanobenzyl)-4,5,6,7-tetrahydrothieno[3,2-c]pyridin-2-yl)acetate (compound I-1) was prepared in this example

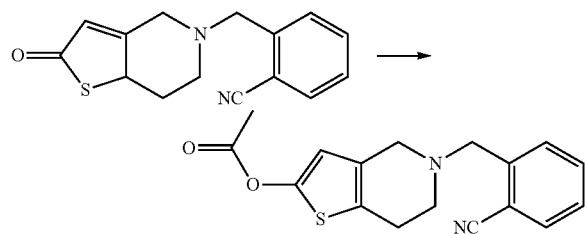

To a reaction flask equipped with a stirrer, a condenser and a thermometer was added 2.7 g of intermediate 1, which was then dissolved in 10 mL dichloromethane. 1.2 g of sodium hydroxide were added to the mixture under stirring. Then the reaction system was cooled to −20° C., and 1.02 g of acetic anhydride was added to the reaction system in batches. After the addition, the reaction mixture was continually stirred at room temperature for 1 h (completion of the reaction was monitored by TLC). Then the reaction mixture was washed with water (3×15 mL). The dichloromethane layer was separated, fully dried over anhydrous sodium sulfate, and filtered. The dichloromethane was evaporated off under reduced pressure, and the residue was purified by a column to obtain a white solid product (HPLC: 99.6%). Rf=0.58 [single point, developing solvent: v (petroleum ether): v (ethyl acetate)=4:1]. 1H NMR (DMSO-d6, 400 MHz)δ: 2.253 (s, 3H), 2.700 (s, 2H), 2.767~2.780 (d, 2H), 3.402 (s, 2H), 3.816 (s, 2H), 6.421 (s, 1H), 7.452~7.489 (t, 1H), 7.606~7.625 (d, 1H), 7.660~7.697 (t, 1H), 7.803~7.822 (d, 1H). MS, m/Z: 312.0 (M).

EXAMPLE 5

(5-(3-cyanobenzyl)-4,5,6,7-tetrahydrothieno[3,2-c]pyridin-2-yl)acetate (compound I-2) was prepared in this example

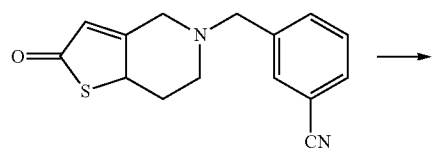

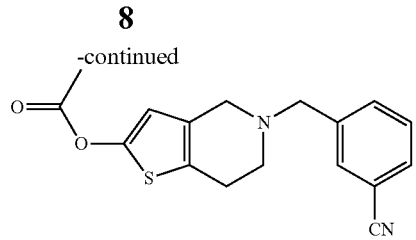

To a reaction flask equipped with a stirrer, a condenser and a thermometer was added 2.7 g of intermediate 2, which was then dissolved in 15 mL trichloromethane. 3.0 g of triethylamine were added to the mixture under stirring. Then the reaction system was cooled to −30° C., and 0.78 g of acetyl chloride was added to the reaction system in batches. After the addition, the reaction mixture was continued to be stirred at 10° C. for 2.5 h (completion of the reaction was monitored by TLC). Then the reaction mixture was washed with water (3×15 mL). The trichloromethane layer was separated, fully dried over anhydrous sodium sulfate, and filtered. The trichloromethane was evaporated off under reduced pressure, and the residue was purified by a column to obtain a white solid product (HPLC: 99.0%). Rf=0.56 [single point, developing solvent: v (petroleum ether): v (ethyl acetate)=4:1]. 1H NMR (DMSO-d6, 400 MHz)δ: 2.255 (s, 3H), 2.701 (s, 2H), 2.769~2.782 (d, 2H), 3.403 (s, 2H), 3.817 (s, 2H), 6.423 (s, 1H), 7.367~7.402 (t, 1H), 7.543~7.561 (d, 1H), 7.632~7.650 (d, 1H), 7.916~7.927 (s, 1H). MS, m/Z: 312.0 (M).

EXAMPLE 6

(5-(4-cyanobenzyl)-4,5,6,7-tetrahydrothieno[3,2-c]pyridin-2-yl)acetate (compound I-3) was prepared in this example

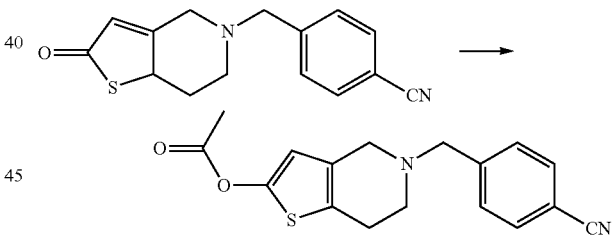

To a reaction flask equipped with a stirrer, a condenser and a thermometer was added 2.7 g of intermediate 3, which was then dissolved in 20 mL toluene. 4.14 g of anhydrous potassium carbonate were added to the mixture under stirring. Then the reaction system was cooled to −10° C., and 0.60 g of acetic acid was added to the reaction system in batches. After the addition, the reaction mixture was continued to be stirred at 30° C. for 3 h (completion of the reaction was monitored by TLC). The reaction mixture was washed with water (3×20 mL). The toluene layer was separated, fully dried over anhydrous sodium sulfate, and filtered. The toluene was evaporated off under reduced pressure, and the residue was purified by a column to obtain a white solid product (HPLC: 99.7%). Rf=0.58 [single point, developing solvent: v (petroleum ether): v (ethyl acetate)=4:1]. 1H NMR (DMSO-d6, 400 MHz) δ: 2.252 (s, 3H), 2.698 (s, 2H), 2.766~2.778 (d, 2H), 3.401 (s, 2H), 3.815 (s, 2H), 6.419 (s, 1H), 7.865~7.889 (d, 2H), 8.021~8.044 (d, 2H). MS, m/Z: 312.0 (M).

EXAMPLE 7

Preparation of hydrochloride of compound I-1 prepared in example 4: 2.0 g of solid product of compound I-1 was dissolved in 10 mL anhydrous diethyl ether. The mixture was cooled to 0° C. in an ice-water bath, and then hydrogen chloride, 15% solution in diethyl ether was added dropwise to the mixture until pH to be 2. The mixture was continually stirred in the ice-water bath for about 1 h, and then filtered to obtain a white solid.

EXAMPLE 8

Preparation of taurate of compound I-2 prepared in example 5: 2.0 g of solid product of compound I-2 was dissolved in 15 mL anhydrous ethanol. The mixture was heated to reflux, and then equimolar taurine was added to the mixture. The mixture was continually stirred at reflux for about 3 h. After the reaction completed, the mixture was stood at room temperature for 24 h, then filtered to obtain a white solid.

EXAMPLE 9

Preparation of sulfate of compound I-3 prepared in example 6: 2.5 g of solid product of compound I-3 was dissolved in 20 mL anhydrous methanol. The mixture was cooled to 5° C. in an ice-water bath, and then concentrated sulfuric acid solution was added dropwise to the mixture until pH to be 3. The mixture was continually stirred in the ice-water bath for about 0.5 h, and then filtered to obtain a white solid.

In order to further sufficiently illustrate the pharmaceutical compositions of the thienopyridine ester derivative containing cyano group of the present invention, following examples 10-13 of preparations are provided. These examples only explain the present invention and do not limit the scope of the present invention. Said preparations could be made from any active compound or salt thereof of the present invention, preferably, said preparations could be made from the compounds prepared by the method of examples 4-6.

EXAMPLE 10

Preparation of hard gelatin capsules using the following ingredients:

|  | Amount/capsule |
|---|---|
| compound I-1 | 75 mg |
| pregelatinized starch | 100 mg |
| Poloxamer | 4 mg |
| sodium carboxymethyl starch | 10 mg |
| magnesium stearate | 20 mg |
| 10% povidone ethanol solution | q.s. |

Preparation process: The ingredients were pre-dried and screened with 100 mesh sieves for use. Then the prescribed doses of the above ingredients were mixed evenly and screened with 60 mesh sieve for 3 times. 10% povidone ethanol (95%) solution (q.s.) was added to the mixture to prepare a wet mass. The wet mass was granulated by passing through an 18 mesh sieve. Drying the obtained granules at 40° C., sizing them by screening with a 16 mesh sieve and then filling them into hard gelatin capsules.

EXAMPLE 11

Preparation of tablets using the following ingredients:

|  | Amount/tablet |
|---|---|
| hydrochloride of compound I-1 | 75 mg |
| starch | 45 mg |
| microcrystalline cellulose | 40 mg |
| sodium carboxymethyl starch | 4.5 mg |
| magnesium stearate | 1 mg |
| talcum powder | 1 mg |
| Poloxamer | 3 mg |

Preparation process: The ingredients were pre-dried and screened with 100 mesh sieves for use. The prescribed doses of the excipients were mixed fully and evenly, then the active ingredient was added into the excipients by incremental dilution method, and the mixture was mixed fully and evenly for 2-3 times after each addition to ensure that the active ingredient and the excipients were mixed well. The mixture was screened with a 20 mesh sieve, and dried at 55° C. in a ventilation oven for 2 h. Sizing the obtained dry granules by screening with a 16 mesh sieve, and the content of the intermediate was tested. After evenly mixed, the granules were compressed into tablets in a tableting machine.

EXAMPLE 12

| Preparation of injections: | |
|---|---|
| taurate of compound I-2 | 45 mg |
| propylene glycol | 100 mg |
| polysorbate 80 | q.s. |
| distilled water | 300 mL |

Preparation method: The active ingredient was added into water for injection dissolving sorbitol and propylene glycol. Medicinal alkali was added to the mixture to adjust pH to be 4-8, so that the active ingredient was dissolved. Active carbon was added to the mixture, stirred and allowed to absorb for 30 min, then the carbon was removed, and the mixture was fine filtrated, filled and sealed, and sterilized.

EXAMPLE 13

| Preparation of lyophilized powder: | |
|---|---|
| sulfate of compound I-3 | 50 mg |
| medicinal alkali | 0.1-7.0% |
| mannitol | 55-80% |

Preparation method: The active ingredient was added into water for injection, and medicinal alkali was added to the mixture to adjust pH to be 4-8, so that the active ingredient was dissolved. Then mannitol was added to the mixture, and the mixture was autoclaved as requested by injections. Active carbon was added to the mixture, and then the mixture was filtered through a millipore filter. The filtrate was packaged separately, and loose lump was produced by freeze-drying method, and then sealed to obtain the product.

The compound of the present invention having the structure of formula I and pharmaceutically acceptable salts thereof have an obvious inhibiting effect on platelet aggregation. The inhibiting effect of the compound of the present invention on rat platelet aggregation is further illustrated by the following pharmacodynamics experiments.

Experiments of Inhibiting Effect on Rat Platelet Aggregation:

1. Experimental Medicines and Reagents:

Compounds I-1, I-2 and I-3, hydrochloride of compound I-1, taurate of compound I-2, and sulfate of compound I-3 as prepared in examples 4-9 are used.

ADP: produced by SIGMA Co.

Sodium carboxymethylcellulose 800-1200: Sinopharm Chemical Reagent Co., Ltd., batch number: F20051103.

2. Experimental Animals:

Wistar rats: SPF grade, male, provided by The Institute of Laboratory Animal Science, Chinese Academy of Medical Sciences, license No. SCXK (jing) 2005-0013.

3. Experimental Instruments:

PAM-3 Dual Channel Platelet Aggregometer: produced by Jiangsu Danyang Radio Factory.

4. Experimental Method and Results:

Healthy male Wistar rats weighing 200-250 g were selected and randomly divided into groups. The experiments were carried out in three batches, and each batch was distributed into a normal control group and 6 compound groups, and totally two dose groups were tested in each batch. The two dose groups set for compounds I-1, I-2 and I-3, hydrochloride of compound I-1, taurate of compound I-2, and sulfate of compound I-3 were 15 mg/kg and 30 mg/kg respectively. Intragastric administration with a dose volume of 10 ml/kg·bw was used. The normal control group was given the same amount of 0.5% CMC-Na. 2 h after administration, 40 mg/kg of pentobarbital sodium was intraperitoneally injected (1 ml/kg) for anesthesia, and blood was collected from the abdominal aorta. 3.8% sodium citrate was used for anticoagulation, and platelet-rich plasma (PRP) and platelet-poor plasma (PPP) were prepared respectively. Maximum percentage of ADP (final concentration: 1.08 μM) induced platelet aggregation was tested on a PAM-3 Dual Channel Platelet Aggregometer.

The experimental results are shown in Table 1 and Table 2.

TABLE 1

Effect of 6 compounds on ADP-induced platelet aggregation ($\bar{X} \pm SD$)

| Groups | Dose (mg/kg) | Number of animals | Maximum percentage of aggregation (%) |
|---|---|---|---|
| Control group | — | 10 | 74.2 ± 20.8 |
| I-1 | 15 | 10 | 20.5 ± 25.5 |
| I-2 | 15 | 10 | 29.8 ± 24.3 |
| I-3 | 15 | 10 | 22.7 ± 24.1 |
| hydrochloride of compound I- | 15 | 10 | 23.6 ± 22.8 |
| taurate of compound I-2 | 15 | 10 | 28.4 ± 23.6 |
| sulfate of compound I-3 | 15 | 10 | 24.3 ± 22.9 |

TABLE 2

Effect of 6 compounds on ADP-induced platelet aggregation ($\bar{X} \pm SD$)

| Groups | Dose (mg/kg) | Number of animals | Maximum percentage of aggregation (%) |
|---|---|---|---|
| Control group | — | 6 | 47.1 ± 14.2 |
| I-1 | 30 | 6 | 8.4 ± 8.3 |
| I-2 | 30 | 6 | 4.9 ± 28.4 |
| I-3 | 30 | 6 | 8.7 ± 17.8 |
| hydrochloride of compound I-1 | 30 | 6 | 7.5 ± 11.6 |
| taurate of compound I-2 | 30 | 6 | 9.4 ± 18.3 |
| sulfate of compound I-3 | 30 | 6 | 6.8 ± 15.6 |

It can be seen from the data of Table 1 and 2 that the compounds of the present invention (15, 30 mg/kg) have an obvious inhibiting effect on ADP-induced platelet aggregation compared to normal control groups. Therefore, the compounds of the present invention can be used for preventing or treating cardiac and cerebral vascular diseases such as coronary artery syndrome, myocardial infarction and myocardial ischemia which are caused by platelet aggregation.

Pharmacokinetic Studies on Animals:

Upon the experiments of intragastric administration on rats, preliminary study results show that compounds I-1, I-2 and I-3, hydrochloride of compound I-1, taurate of compound I-2, and sulfate of compound I-3 of the present invention and a commercial medicine Clopidogrel are all prodrugs, and they need to be converted into active metabolites thiols in vivo under the actions of related enzymes, so as to achieve the therapeutic effect. However, the conversion rate of the compounds I-1, I-2 and I-3, hydrochloride of compound I-1, taurate of compound I-2, and sulfate of compound I-3 are about 5 times higher than Clopidogrel, and the time to peak concentration of their active metabolites are from 50 min to 1 h, which are also faster than that of Clopidogrel. Therefore, the compounds of the present invention are likely to be further developed into antiplatelet medicine with a faster onset of action.

Two Weeks of Toxicity Studies on Rats (Compared with Clopidogrel)

Materials and Methods:

Compounds for testing: compound I-1 and Clopidogrel.

Preparation of Solution: compound I-1 is grinded with 0.5% CMC-Na and corn oil, then dissolved under ultrasonic condition. 100 mg/ml suspension is prepared before use, and administrated intragastricly at 1 ml/100 g every morning.

Experimental animals: SD rats weighing about 180 g, 7 female and 7 male in each group.

Grouping and dose regimen: compound I-1 is administrated intragastricly at a dose of 1000 mg/kg once a day for 2 weeks. The same amount of solvent is administrated intragastricly to the blank control group, and equal-dose (1000 mg/kg) of Clopidogrel is administrated intragastricly to the positive control group.

Experimental Results:

Death of rats occurs in all medicated groups during the entire testing period, the specific number and time of death are shown in Table 3. From the third day of intragastric administration, hemorrhagic secretions around the rats' nasal can be observed in both the compound I-1 group and the Clopidogrel group, but it is obviously slight in the compound I-1 group than in the Clopidogrel group.

TABLE 3

| Groups | Female rats (N = 7) | | Male rats (N = 7) | |
|---|---|---|---|---|
|  | Number of deaths | time | Number of deaths | time |
| Blank control group | 0 | — | 0 | — |
| Compound I-1 group | 1 | T4 | 0 | — |
| Clopidogrel group | 2 | T4\T5 | 1 | T8 |

What is claimed is:

1. A compound with the structure of formula I or a pharmaceutically acceptable salt thereof:

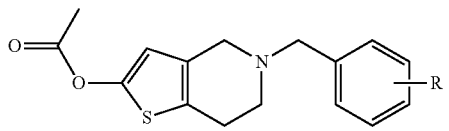

wherein, R is cyano group, and the compound is selected from one of the following compounds:
- I-1: 5-(2-cyanobenzyl)-4,5,6,7-tetrahydrothieno[3,2-c]pyridin-2-yl acetate;
- I-2: 5-(3-cyanobenzyl)-4,5,6,7-tetrahydrothieno[3,2-c]pyridin-2-yl acetate;
- I-3: 5-(4-cyanobenzyl)-4,5,6,7-tetrahydrothieno[3,2-c]pyridin-2-yl acetate.

2. The compound with the structure of formula I or a pharmaceutically acceptable salt thereof according to claim 1, wherein the pharmaceutically acceptable salt comprises the salt formed by the compound of formula I with an inorganic acid or an organic acid.

3. The compound with the structure of formula I or a pharmaceutically acceptable salt thereof according to claim 2, wherein the pharmaceutically acceptable salt is selected from hydrochlorides, hydrobromides, hydriodates, sulfates, hydrosulfates, phosphates, hydrophosphates, acetates, propionates, butyrates, lactates, mesylates, tosilates, maleates, benzoates, succinates, tartrates, citrates, fumarates, taurates, gluconates, and amino acid salts of the compound of formula I.

4. A pharmaceutical composition for antiplatelet aggregation, wherein, the pharmaceutical composition comprises a therapeutically effective amount of the compound with the structure of formula I or a pharmaceutically acceptable salt thereof according to claim 1, and a pharmaceutically acceptable carrier and/or excipient.

5. The pharmaceutical composition according to claim 4, wherein the pharmaceutical composition is a solid oral preparation, a liquid oral preparation or an injection.

* * * * *